US00PP18414P3

(12) United States Plant Patent
Cunneen

(10) Patent No.: US PP18,414 P3
(45) Date of Patent: Jan. 8, 2008

(54) *ARGYRANTHEMUM* PLANT NAMED 'COTTON CANDY'

(50) Latin Name: *Argyranthemum frutescens*
Varietal Denomination: Cotton Candy

(75) Inventor: Thomas M. Cunneen, Balmoral Village (AU)

(73) Assignee: Amerinova Properties, LLC, Bonsall, CA (US)

( * ) Notice: Subject to any disclaimer, the term of this patent is extended or adjusted under 35 U.S.C. 154(b) by 0 days.

(21) Appl. No.: 11/445,621

(22) Filed: Jun. 2, 2006

(65) Prior Publication Data

US 2007/0283469 P1 Dec. 6, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell

(57) ABSTRACT

A new and distinct cultivar of *Argyranthemum* plant named 'Cotton Candy', particularly characterized by its mounded, decorative inflorescence type in which the ray florets become progressively shorter in length toward the center to produce a ruffled appearance and a mounded effect, light-pink inflorescence color, dense flowering on short stems, and compact growing habit.

1 Drawing Sheet

The present invention relates to a new and distinct cultivar of *Argyranthemum* plant, botanically known as *Argyranthemum frutescens,* and referred to by the variety denomination 'Cotton Candy'.

The new cultivar is the product of a planned breeding program carried out by the inventor in Balmoral Village, New South Wales, Australia. The new cultivar is the result of a cross made by the inventor on Sep. 10, 2002, and was discovered in the same location by the inventor in March 2003 as a seedling growing among other seedling plants of the cross. The female parent is proprietary, and identified by the code number SLX01020.1. The male parent is also proprietary, and identified by the code number SLX01005.22. Neither parent is patented.

The first act of asexual reproduction of the new cultivar was accomplished by vegetative cuttings in March 2003 in a controlled environment in Balmoral Village, New South Wales, Australia. The new cultivar has been successfully propagated by both vegetative cuttings and tissue culture. Horticultural examination of controlled flowerings of successive plantings through at least eight generations has shown that the unique combination of characteristics of the new cultivar are firmly fixed and are retained through successive generations of asexual reproduction.

The new cultivar has not been observed under all possible environmental conditions. The phenotype may vary significantly with variations in environment, such as temperature, light intensity, and daylength without, however, any variance in genotype. The following observations, measurements, and comparisons describe plants grown in New South Wales, Australia, and Bonsall, Calif., under normal commercial growing conditions.

SUMMARY OF THE INVENTION

The following traits have been repeatedly observed and have been determined to be basic characteristics of the new cultivar, which, in combination, distinguish the new cultivar as being new and distinct:

1. The inflorescences are in the form of a mounded decorative in which the more central rays are much shorter, centrally defining a very small central disc. Overall, the inflorescences have a ruffled appearance.
2. The plant habit is very compact.
3. The foliage is very dense due to the large number of secondary and tertiary shoots which are formed. The leaves are narrow and finely dissected to accommodate the dense foliage.
4. The inflorescence stems are short.
5. Floriferous habit.
6. The inflorescence color when the inflorescences open is a very light pink, darkening somewhat as the flowers fully open.

The new cultivar is distinguished from its female parent by its ruffled inflorescence type, compact growth habit, and pink inflorescence color. The female parent has an anemone inflorescence type, open growth habit, and white inflorescence color. The male parent has a single inflorescence type and red inflorescence color.

The new cultivar can also be compared to the cultivar 'Summer Stars Pink', disclosed in U.S. Plant Pat. No. 11,939 and characterized by its medium plant height and long inflorescence stems. By contrast, 'Cotton Candy' is very compact and has short stems. The inflorescence type and color of the respective cultivars are similar.

'Cotton Candy' is distinguished in a similar manner from the Cultivar OHARO1245, disclosed in U.S. Plant Pat. No. 16,283 and known commercially under the name 'Madeira Double Pink'. The comparison cultivar has a tall plant height and long inflorescence stems, compared to the compact habit and short stems of 'Cotton Candy'. In addition, the inflorescence color of 'Cotton Candy' is a darker pink. The flower shapes of the respective cultivars are similar.

BRIEF DESCRIPTION OF THE PHOTOGRAPHIC DRAWINGS

The photograph at the bottom of the sheet shows a front-perspective view of a typical flowering plant of the new cultivar.

The photo at the top of the sheet comprises a close-up view showing inflorescences just opening and fully open.

The colors in the photographs are as true as is reasonably possible to obtain with colored reproductions of this type. The color values stated below in the detailed description are accurate.

DETAILED BOTANICAL DESCRIPTION

In the following description, color references are made to The Royal Horticultural Society Colour Chart. The values are based on plant material grown in Bonsall, Calif.

Botanical classification: *Argyranthemum frutescens* cv 'Cotton Candy'.

*Parentage.*—Seed parent: SLX01020.1. Pollen parent: SLX01005.22.

Propagation:

*Type.*—By leaf cuttings and by tissue culture.

*Time and temperature to initiate roots.*—Approximately 7 to 10 days at 20 degrees Centigrade. A rooted cutting is produced in approximately 28 to 32 days at 20 degrees Centigrade.

Root description: Fibrous, moderately thick, white in color.

Rooting habit: Very dense, freely branching.

Plant description:

*General appearance.*—Upright but compact, mounded, with a uniform canopy; a ball of inflorescences.

*Shape.*—Round.

*Habit.*—'Cotton Candy' is a very compact plant with many laterals and dense, needle-like foliage; nice, short, tidy plant shape.

*Plant height.*—27 cm.

*Plant diameter.*—34 cm.

*Lateral branching.*—Very free-branching. Laterals spiral up main stem from nearly every node. Secondary laterals also have many tertiary laterals. Number of primary lateral branches: 20. Number of secondary lateral branches: Each has about 6-8 tertiary shoots. Length of primary branches: About 14 cm to 24 cm. Diameter: About 0.4 cm to 0.5 cm.

*Internode length.*—About 1.5 cm to 2.0 cm.

*Texture.*—Smooth, woody at base.

*Color.*—147C when young; 199B for bark on woody stem.

*Foliage.*—Generally flat, finely dissected and very dense.

*Arrangement.*—Alternate.

*Simple or compound.*—Simple.

*Length.*—About 3.0 cm to 4.5 cm.

*Width.*—About 2.0 cm to 2.7 cm.

*Shape.*—Finely dissected with 5-7 narrow lobes.

*Sinuses.*—Parallel.

*Apex.*—Acute.

*Base.*—Attenuate.

*Margin.*—Entire, but with deep sinuses.

*Texture.*—Smooth and glabrous.

*Color.*—Immature; upper surface, 147A. Lower surface, 147B. Mature; upper surface, 147A. Lower surface, 147B.

Venation: 147B on both upper and lower surfaces.

*Petiole.*—Length: 1.0 cm. to 1.5 cm. Diameter: 0.2 cm. Color, upper surface, 147C. Lower surface, 147D.

Other foliage characteristics: Leaves are narrow, finely dissected, and very dense due to the large number of secondary and tertiary shoots. Leaf surfaces have a slightly waxy cuticle, which morphologically suggests drought tolerance.

Inflorescence:

*In general.*—Not a true daisy, but a small, mounded multiplex decorative with significantly reduced central rays that progress to a very tiny central disc.

*Type.*—Multiplex decorative.

*Orientation.*—Upright on terminal stem and tending to curl upright on peduncle of lateral shoots.

*Longevity.*—3-4 weeks.

*Fragrance.*—None.

*Quantity.*—About 12 open inflorescences and 10 buds per lateral stem.

*Size.*—Total diameter: About 4 cm. Depth: 1.2 cm.

*Diameter of disc.*—The very tiny central disc results in a multiplex decorative type with a burgundy eye, the color of immature disc florets. The eye tends to disappear as the inflorescence ages and the disc florets open.

*Receptacle.*—Diameter, 1.6 cm. Height, 0.5 cm.

Buds (just before anthesis):

*Height.*—1.0 cm.

Shape: Rounded but with a flat top.

Color: 157C.

Ray florets:

*Quantity per flower.*—About 146.

*Shape.*—Ligulate. Length: Highly variable due to inflorescence type. Outer rays, approximately 1.8 cm. Inner rays, about 0.7 cm. Width: Also variable; outer and inner rays approximately 0.5 cm and 0.25 cm, respectively. Apex: Minutely tridentate. Base: Acute. Margin: Entire. Texture: Smooth, velvety.

*Aspect.*—When inflorescences are young, ray florets lay flat, but as inflorescence ages, older rays reflex backward as the smaller center rays stand up with a sort of corona effect. This produces a deeper, mounded display.

*Color.*—When opening: Upper surface, 65C at tips. Lower surface, whiter than 155D. Mature: Upper surface, 73C. Lower surface, 73D.

Other comments: Between disc florets and flat ligulate ray florets there are approximately 3 whorls of transitional florets (about 40 in all) that are tiny and tubular but with small, flat, ray-like tabs.

Disc florets:

*Quantity.*—Approximately 28.

*Shape.*—Tubular. Apex: 5-tipped. Base: Fused into tube.

*Length.*—0.3 cm.

*Diameter.*—0.1 cm.

*Color.*—Immature 183A. Mature, lighter than 73D.

Involucral bracts:

*Quantity.*—About 24.

*Length.*—0.4 cm.

*Width.*—0.2 cm.

*Shape.*—Elliptical.

*Apex.*—Acute.

*Base.*—Truncate.

*Margin.*—Entire, curved.

*Color.*—Upper surface 147C. Lower surface 146B.

Peduncle:

*Strength.*—Good.

*Aspect.*—Terminal is upright. Laterals, 45-60 degrees from vertical.

*Length.*—Terminal peduncle, 8 cm. Fourth peduncle, 5.4 cm.

*Diameter.*—About 0.15 cm.

*Texture.*—Smooth, longitudinally ridged.

*Color.*—146C.

Reproductive organs:

*Stamens.*—Not apparent on tiny disc florets. The new cultivar is functionally sterile.

*Pistils.*—On ray florets only; one per ray floret; 0.6 cm on largest ray floret.

*Stigmas.*—Bipartite shape. Color, 163B.

*Styles.*—Length, 0.3 cm. Color, 145C.

Other inflorescence characteristics: The ray florets are highly variable in size, becoming progressively smaller toward the center. The larger and medium-sized rays lie flat when young, but reflex back with age. The smaller center rays tend to stand upright and are a little curly. These have burgundy tips when young and are displaced when the disc florets open. All of these characteristics produce a mounded inflorescence, with the flowering being prolific and held above dense foliage. Since the habit is very compact, the effect is nearly a ball of mounded inflorescences.

It is claimed:

1. A new and distinct cultivar of *Argyranthemum* plant named 'Cotton Candy', as illustrated and described.

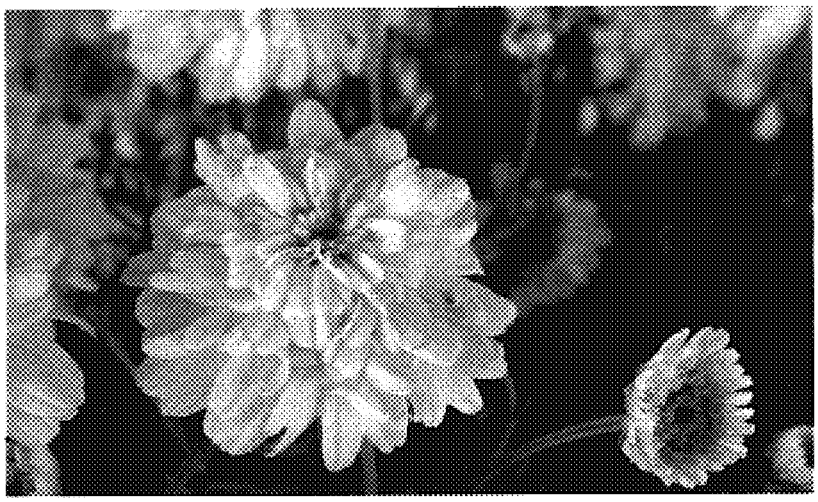
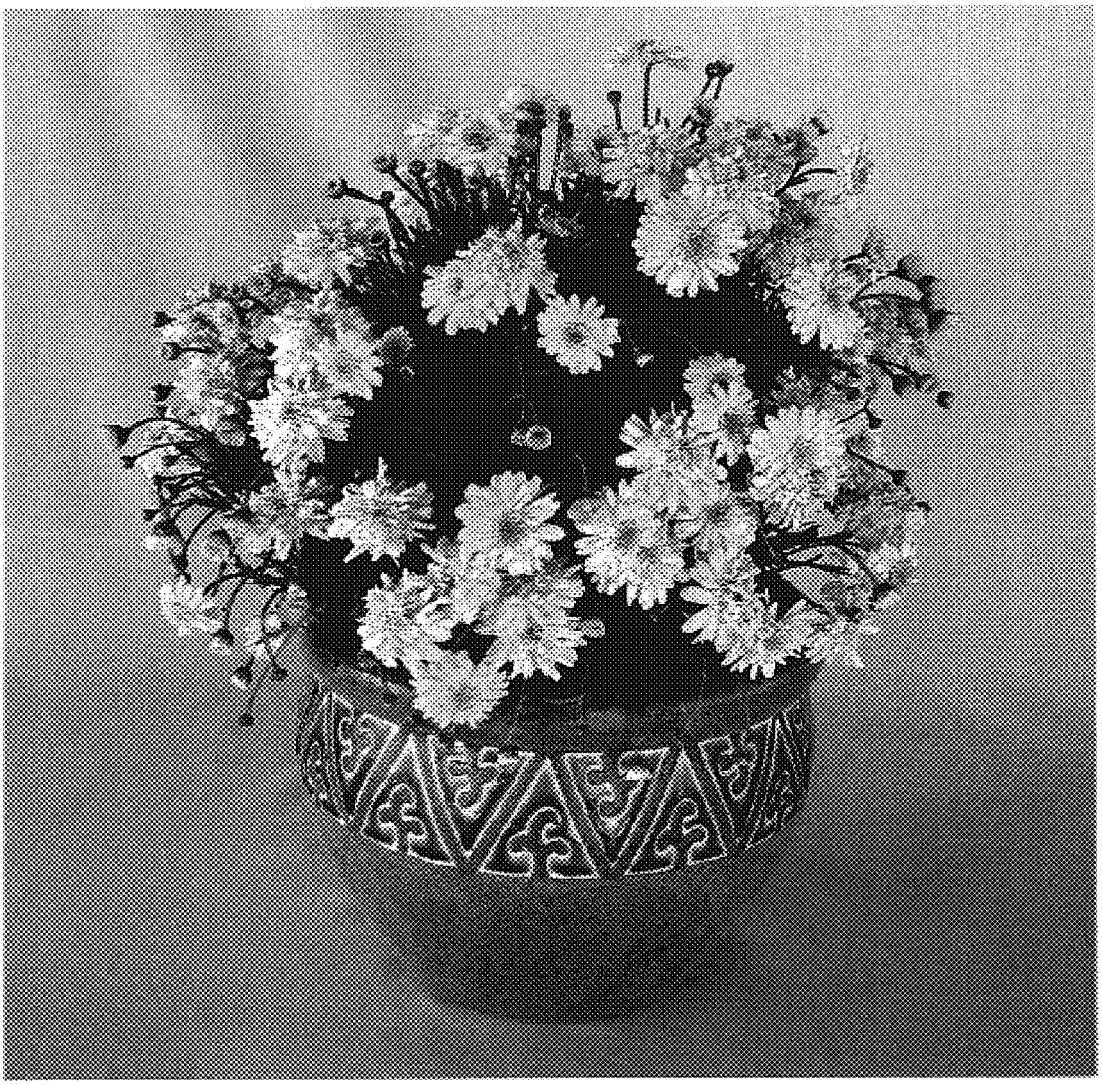

* * * * *